(12) United States Patent
Hestad

(10) Patent No.: US 7,648,521 B2
(45) Date of Patent: Jan. 19, 2010

(54) SYSTEM AND METHOD FOR MINIMALLY INVASIVE SPINAL SURGERY

(75) Inventor: Hugh D. Hestad, Edina, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 265 days.

(21) Appl. No.: 11/686,453

(22) Filed: Mar. 15, 2007

(65) Prior Publication Data

US 2008/0228184 A1 Sep. 18, 2008

(51) Int. Cl.
*A61B 17/70* (2006.01)

(52) U.S. Cl. .................. 606/246; 606/60; 606/249; 606/250; 606/263

(58) Field of Classification Search .............. 606/54, 606/61, 86, 246, 249–279
See application file for complete search history.

(56) References Cited

U.S. PATENT DOCUMENTS

| | | | |
|---|---|---|---|
| 5,047,055 A | 9/1991 | Bao et al. | |
| 5,171,281 A | 12/1992 | Parsons et al. | |
| 5,242,443 A | 9/1993 | Kambin | |
| 5,314,478 A | 5/1994 | Oka et al. | |
| 5,458,643 A | 10/1995 | Oka et al. | |
| 6,235,028 B1 | 5/2001 | Brumfield et al. | |
| 6,402,784 B1 | 6/2002 | Wardlaw | |
| 6,520,907 B1 | 2/2003 | Foley et al. | |
| 6,530,929 B1 | 3/2003 | Justis et al. | |
| 6,569,442 B2 | 5/2003 | Gan et al. | |
| 6,596,008 B1 | 7/2003 | Kambin | |
| 6,726,721 B2 | 4/2004 | Stoy et al. | |
| 6,733,531 B1 | 5/2004 | Trieu | |
| 6,821,277 B2 | 11/2004 | Teitelbaum | |
| 6,951,538 B2 | 10/2005 | Ritland | |
| 7,008,424 B2 | 3/2006 | Teitelbaum | |
| 2002/0082523 A1* | 6/2002 | Kinsella et al. | ............. 600/585 |
| 2003/0120345 A1 | 6/2003 | Cauthen | |
| 2004/0039384 A1 | 2/2004 | Boehm, Jr. et al. | |
| 2004/0138662 A1 | 7/2004 | Landry et al. | |
| 2004/0143265 A1 | 7/2004 | Landry et al. | |
| 2004/0172022 A1 | 9/2004 | Landry et al. | |
| 2005/0065517 A1 | 3/2005 | Chin | |

(Continued)

OTHER PUBLICATIONS

Zimmer Spine, Silhouette Spinal Fixation System, Catalog, Mar. 2005, 6 pgs.

*Primary Examiner*—Eduardo C Robert
*Assistant Examiner*—Christina Negrelli
(74) *Attorney, Agent, or Firm*—Crompton, Seager & Tufte, LLC.

(57) ABSTRACT

A system for installing a cross member between first and second anchor members within a patient's body generally includes first and second docking members configured to be removably coupled to the respective first and second anchor members. Each docking member has a first end with an opening, a second end, and a body extending between the first and second ends. The body includes an outer surface with an opening, and a bore extends from the opening on the first end of the body to the opening on the outer surface. The openings on the outer surface of each docking member are configured to be aligned so that the bore in the first docking member is able to direct a wire member into the bore in the second docking member. A method for minimally invasive surgery using the system is also disclosed.

21 Claims, 3 Drawing Sheets

U.S. PATENT DOCUMENTS

| | | |
|---|---|---|
| 2005/0131408 A1 | 6/2005 | Sicvol et al. |
| 2005/0131421 A1 | 6/2005 | Anderson et al. |
| 2005/0192589 A1 | 9/2005 | Raymond et al. |
| 2005/0215999 A1 | 9/2005 | Birkmeyer et al. |
| 2005/0228380 A1 | 10/2005 | Moore et al. |
| 2005/0234449 A1 | 10/2005 | Aferzon |
| 2006/0247630 A1 * | 11/2006 | Iott et al. ............... 606/61 |
| 2007/0288026 A1 | 12/2007 | Shluzas |
| 2007/0299443 A1 | 12/2007 | DiPoto et al. |
| 2007/0299444 A1 | 12/2007 | DiPoto et al. |
| 2008/0015582 A1 | 1/2008 | DiPoto et al. |

* cited by examiner

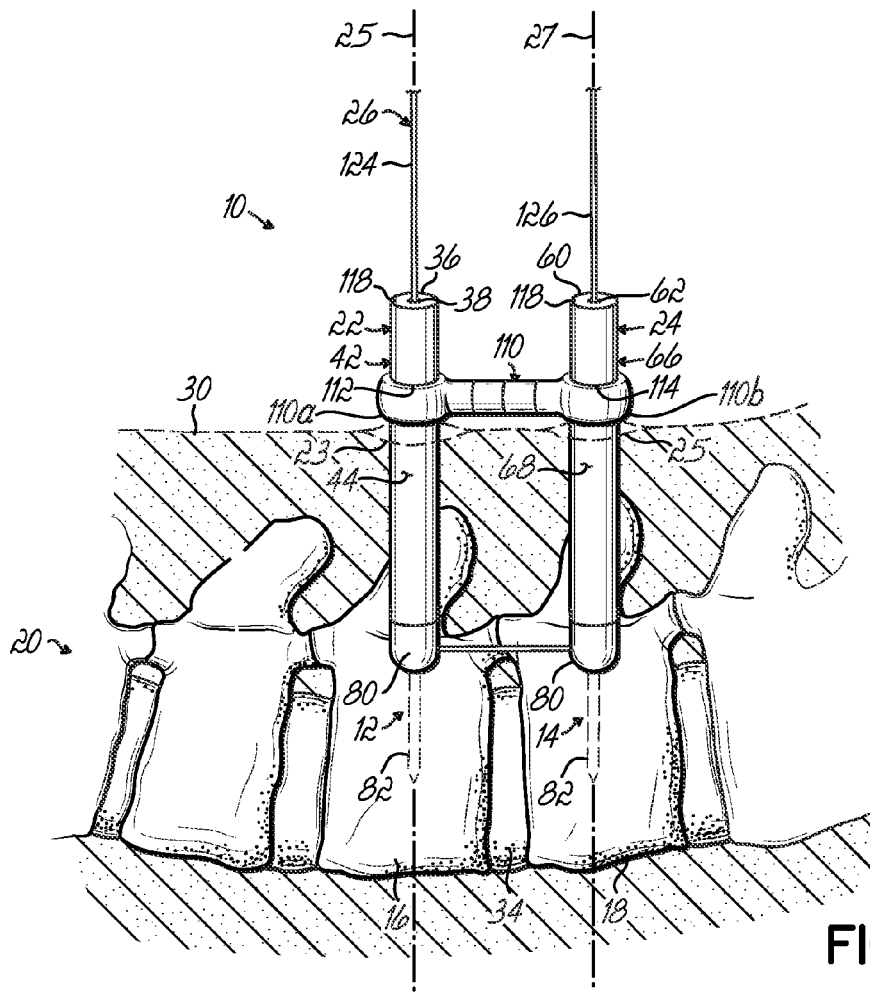
FIG. 1
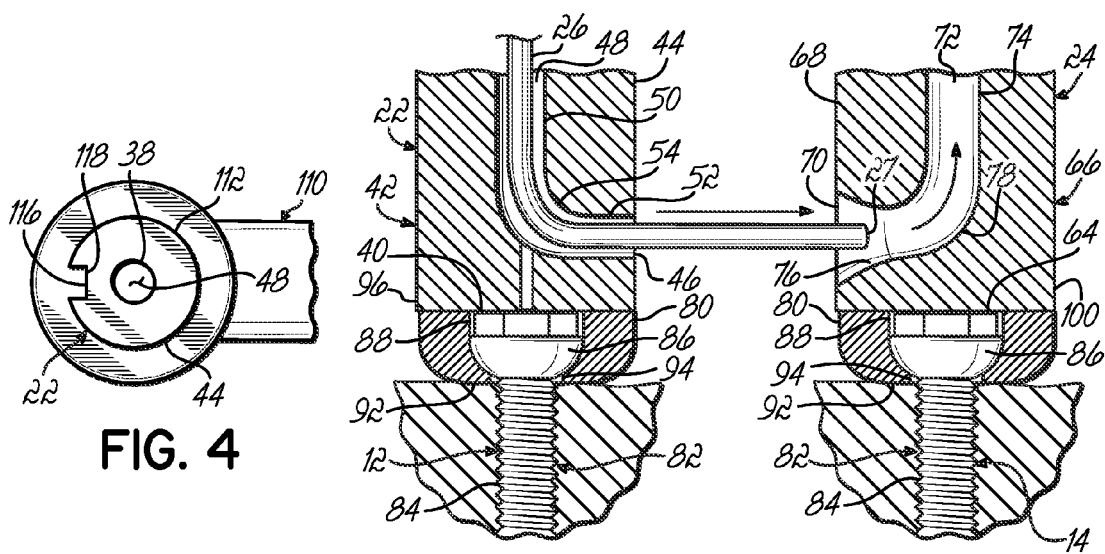
FIG. 4
FIG. 3

SYSTEM AND METHOD FOR MINIMALLY INVASIVE SPINAL SURGERY

FIELD OF THE INVENTION

This invention relates generally to surgical systems and methods, and more particularly to a system and method for minimally invasive spinal surgery.

BACKGROUND

The spinal column is a highly complex system of bones and connective tissues that provides support for the body and protects the delicate spinal flexible connecting member and nerves. The spinal column includes a series of vertebrae stacked one on top of the other, each vertebral body including an inner or central portion of relatively weak cancellous bone and an outer portion of relatively strong cortical bone. Situated between each vertebral body is an intervertebral disc that cushions and dampens compressive forces experienced by the spinal column. A vertebral canal containing the spinal flexible connecting member and nerves is located behind the vertebral bodies.

There are many types of spinal column disorders including scoliosis (abnormal lateral curvature of the spine), kyphosis (abnormal forward curvature of the spine, usually in the thoracic spine), excess lordosis (abnormal backward curvature of the spine, usually in the lumbar spine), spondylolisthesis (forward displacement of one vertebra over another, usually in a lumbar or cervical spine) and other disorders caused by abnormalities, disease, or trauma, such as ruptured or slipped discs, degenerative disc disease, fractured vertebra, and the like. Patients that suffer from such conditions usually experience extreme and debilitating pain as well as diminished range of motion and nerve function. These spinal disorders may also threaten the critical elements of the nervous system housed within the spinal column.

A variety of systems have been developed to stabilize and correct spinal deformities. Many of the systems achieve immobilization by implanting artificial assemblies in or on the spinal column. Lateral and anterior assemblies are typically coupled to the anterior portion of the spine. Posterior implants generally comprise pairs of rods that are aligned along the axis with which the bones are to be disposed. The rods are typically attached to the spinal column by anchor members, such as hooks coupled to the lamina or to the transverse processes, or screws inserted through the pedicles.

One problem with surgically accessing the spine to deal with these disorders is that the skin and tissue surrounding the surgical site must be cut, removed, and/or repositioned to gain access to the location where the devices are to be installed. This is particularly true when installing posterior implants designed to facilitate fusion at various levels of the spine. For example, to install a fixation rod between two pedicle screws, a first pedicle screw is typically secured within the patient's body at one level of the spine and a second pedicle screw typically secured at another level. Sometimes separate access holes or channels are established for each screw and the fixation rod is then maneuvered within the patient's body through the tissue between the two screws. The tools and/or space required to properly position the fixation rod may require significant cutting or repositioning of skin and tissue, which often results in damage, scarring, and longer recovery times. Often, three or more incisions may be necessary for implantation of pedicle screws and the fixation rod.

Various minimally invasive surgical systems have been developed to address these concerns. For example, U.S. patent application Ser. No. 11/228,958 ("the '958 patent"), entitled "Apparatus and Method for Minimally Invasive Spine Surgery" and assigned to the assignee of the present invention, discloses a system in which at least two docking members are configured to align transverse bores provided in two associated pedicle screws. FIG. 9 of the '958 application illustrates an embodiment in which the docking members include a bore or lumen for guiding a therapeutic device, such as a fixation rod, to the pedicle screws. Other approaches to reducing trauma include inserting expandable retractors through a relatively small incision on the patient's body. Once expanded, such retractors may provide access to more than one vertebral level.

These systems and methods may help reduce the amount of manipulation or disruption of tissue. Additional minimally invasive techniques are highly desirable because they may reduce blood loss and scarring, and result in less post-operative pain and shorter recovery times.

SUMMARY OF THE INVENTION

This invention provides a system and method for minimally invasive surgery. The invention is particularly applicable to spinal surgery procedures requiring a cross member to be installed between first and second anchor members within a patient's body, although other applications are possible.

In one embodiment, the system generally includes first and second docking members configured to be removably coupled to the first and second anchor members substantially along respective axes. Each docking member has a first end with an opening, a second end, and a body extending between the first and second ends. The body includes an outer surface with an opening proximate the second end. A bore provided in each docking member extends from the opening on the first end to the opening on the outer surface. Thus, the bore may have an axial portion extending from the first end toward the second end and a transverse portion extending from the axial portion to the opening on the outer surface.

The opening on the outer surface of the first docking member is configured to be aligned with the opening on the outer surface of the second docking member. Additionally, the bore in the first docking member is configured to direct a wire member, such as a guidewire, from the opening on the first end, through the body, and out the opening on the outer surface toward the opening on the outer surface of the second docking member. The wire member, which is received by the bore in the second docking member, ultimately serves to guide the cross member into the patient's body between the first and second anchor members.

A connection member may be provided with the system to facilitate alignment of the openings on the outer surface of each docking member. In particular, a connection member may be removably coupled to both the first and second docking members so as to extend between the docking members. In one embodiment, the connection member includes first and second receiving bores configured to slide over the respective first and second docking members. The first and second receiving bores each have a key, and the outer surface of each docking member each has a groove configured to cooperate with the corresponding key to prevent relative rotation between the docking member and connection member.

A method for minimally invasive surgery using the first and second docking members is also provided. The method generally includes creating first and second access channels extending to respective first and second locations within a patient's body. After inserting first and second anchor members in the patient's body through the respective first and second access channels, the first and second docking members are inserted through the respective first and second access channels until each docking member is received by the corresponding anchor member. The opening on the outer surface of the first docking member is aligned with the opening on the outer surface of the second docking member, and a wire member is then inserted into the first access channel, through the bore in the first docking member, into the bore of the second docking member, and out of the second access channel.

In one embodiment, the method further includes removing the first and second docking members while maintaining the wire member within the patient's body. A cross member, such as a spinal fixation rod or flexible cord, is then guided over the wire member until the cross member extends between the first and second anchor members. At this point, the cross member may then be secured to the first and second anchor members.

BRIEF DESCRIPTION OF THE DRAWINGS

The accompanying drawings, which are incorporated in and constitute a part of this specification, illustrate exemplary embodiments of the invention and, together with a general description of the invention given above, and the detailed description given below, serve to explain the principles of the invention.

FIG. 1 is a schematic view of a minimally invasive surgery system according to one embodiment of the invention;

FIG. 3 is a cross-sectional view showing a wire member inserted through first and second docking members of the system shown in FIG. 1;

FIG. 4 is a top plan view of a portion of the system shown in FIG. 1;

DETAILED DESCRIPTION

Figure 2:
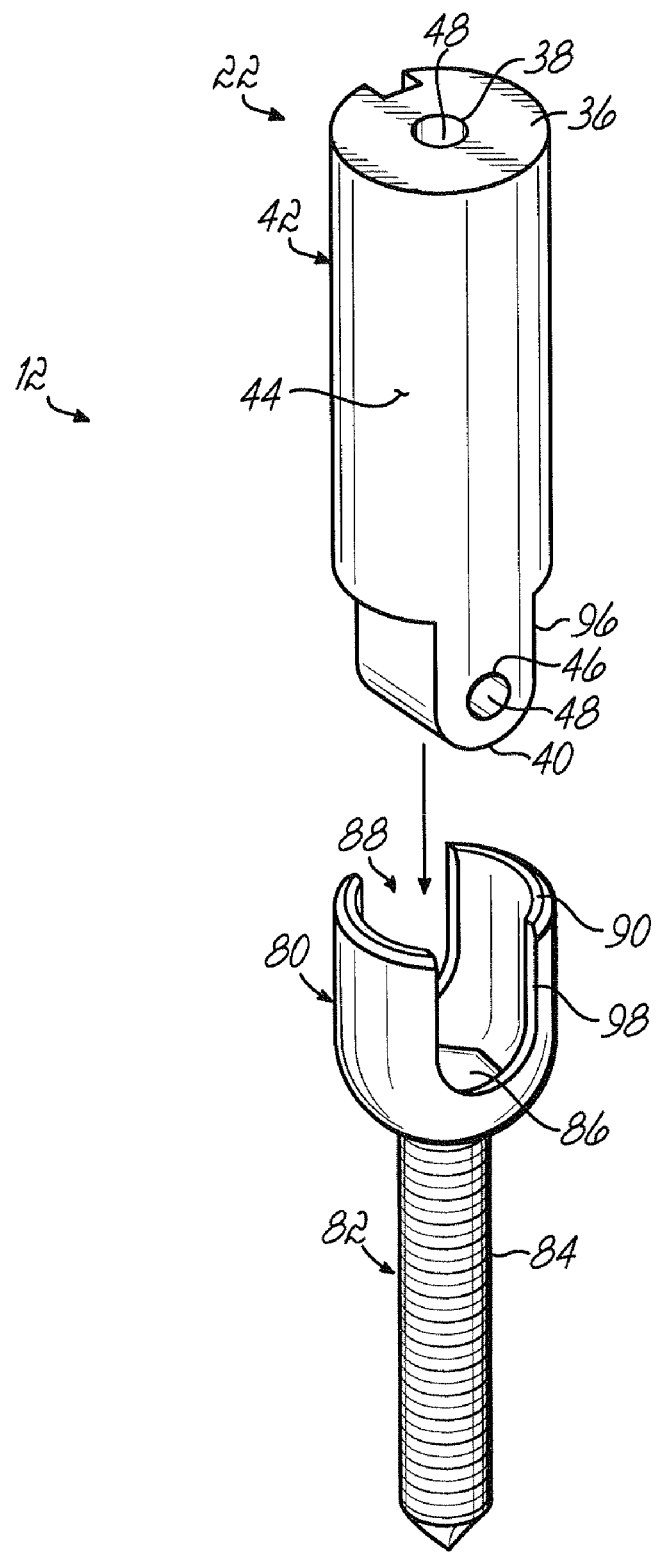
FIG. 2 is perspective view showing a first docking member and first anchor member of the system shown in FIG. 1.

FIG. 1 shows one embodiment of a minimally invasive surgical system lo according to the invention. The system lo may be used for a variety of surgical procedures, but will described below primarily with reference to spinal surgery procedures. In particular, the system lo will be described with reference to spinal fusion techniques in which first and second anchor members 12, 14 are secured to adjacent vertebrae 16, 18 of a spine 20.

To this end, the system lo includes first and second docking members 22, 24 configured to be passed through two incisions 23, 25, respectively, to be removably coupled to the first and second anchor members 12, 14 within a body 30 substantially along respective first and second axes 25, 27. The first and second docking members 22, 24 are also configured to facilitate the insertion of a wire member 26, such as a guidewire 26, into the body 30. As will be described in greater detail below, the wire member 26 serves to direct a cross member 32 (FIGS. 5 and 6), such as a rod or flexible construct, into the body 30 between the first and second anchor members 12, 14. The cross member 32 cooperates with the anchor members 12, 14 to help stabilize the spine 20 so that fusion may occur at a disc space 34 between the adjacent vertebrae 16, 18, as known in the art. Additionally, the cross member 32 may include a leading end 33 shaped to improve its passage through tissue, such as a cone or rounded shape. In other embodiments, the leading end 33 of the cross member 32 can have a flat leading end.

FIGS. 2-3 illustrate one embodiment of the first anchor member 12 and first docking member 22 in further detail. The first docking member 22 includes a first end 36 having an opening 38, a second end 40, and a body 42 extending between the first and second ends 36, 40. The body 42 may be cylindrical in nature and further includes an outer surface 44 with an opening 46 proximate the second end 40. A bore 48 provided in the first docking member 22 extends from the opening 38 on the first end 36 to the opening 46 on the outer surface 44. In the exemplary embodiment shown in the figures, the bore 48 has an axial portion 50 extending from the first end 36 toward the second end 40 and a transverse portion 52 extending from the axial portion 50 to the opening 46 on the outer surface 44. A curved transition portion 54 joins the axial portion 50 to the transverse portion 52, which may be substantially perpendicular to each other.

The second docking member 24 in one embodiment also includes a first end 60 having an opening 62, a second end 64, and a body 66 extending between the first and second ends 60, 64. The body 66, like the body 42, includes an outer surface 68 with an opening 70, and a bore 72 extends through the body 66 from the opening 62 to the opening 70. If desired, the second docking member 24 may have substantially the same configuration as the first docking member 22. For example, the bore 72 may also be defined by an axial portion 74 extending from the first end 60 toward the second end 64, a transverse portion 76 extending from the axial portion 74 to the opening 70, and a curved transition portion 78 between the axial and transverse portions 74, 76. The second docking member 24 may alternatively have a different configuration than the first docking member 22. For example, in a manner not shown herein, the second docking member 24 may simply be a cannula with opening on an outer surface extending into the cannula. Those skilled in the art will appreciate that a number of different configurations are possible for each of the first and second docking members 22, 24.

The first and second docking members 22, 24 may also be configured to be received by the respective first and second anchor members 12, 14. To this end, the first and second anchor members 12, 14 may each include a cup-shaped retainer or yoke member 80 and a pedicle screw 82 having a shaft portion 84 and an enlarged head portion 86. The retainers 80 each define a socket 88 having an open top end go and a bottom end 92 with a bore 94, which is sized to retain the head portion 86 of the pedicle screw 82 within the socket 88 while allowing the shaft portion 84 to extend there through. As shown in FIG. 2, the first docking member may include a bottom portion 96 at the second end 40 configured to be received in the socket 88. Because the transverse portion 52 of the bore 48 is positioned within the bottom portion 96, the retainer 80 includes one or more cut-out portions or slots 98 so that the retainer 80 does not block the opening 46 on the outer surface 44. The second docking member 24 may also include a bottom portion 100 configured to cooperate with the second anchor member 14 in a similar manner.

With reference to FIG. 3, the opening 46 on the first docking member 22 is configured to be aligned with the opening 70 on the second docking member 24. In the exemplary embodiment, the openings 46 and 70 are generally aligned in a cephalo-caudal relationship. Additionally, the bore 48 is configured to direct the wire member 26 from the opening 38 in a direction generally perpendicular to the axis of rotation of the spine, through the body 42, and out the opening 46 in a controlled manner toward the opening 70 on the second docking member 24, where the wire member 26 is ultimately received. In the exemplary embodiment, the diameter of the wire member 26 is less than the diameter of the bore 48 to allow some maneuvering or manipulation of the wire member 26. Alternatively, the wire member 26 and bore 48 can be configured to have a close diameter tolerance. The wire member 26 must therefore be capable of being bent as it is advanced through the bore 48 yet maintain sufficient rigidity to be forced through any tissue positioned between the first and second docking members 22, 24. For example, in one embodiment, the wire member 26 may be a guidewire formed from nickel titanium (NiTi) that has been annealed in a straightened form. In another embodiment, the wire member 26 may an SST coiled wire with a straight core, such as those commonly used in cardiology. In yet a further embodiment, the wire member 26 may be formed from shape memory material, a polymeric material, such as a polymeric cord or any other suitable material and may have any suitable cross-sectional shape, such as circular, oval, rectangular, square or other polygonal shape.

The opening 70 in the second docking member 24 may be flared to facilitate receiving the wire member 26 after it is advanced through the first docking member 22. Alternatively, the opening 70 can be sized larger than the opening 46 and not include a flared wire member 26 receiving portion. Once received, the wire member 26 may be guided through the second docking member 24 by the bore 72 and out the opening 62. If the second docking member 24 is simply a cannula, various manipulation tools (not shown) may be required to reach into the cannula and pull the wire member 26 through the second docking member 24 after the wire member 26 is received in the opening 70.

To align and maintain the openings 46 and 70, the system lo may further include a connection member 110 (FIGS. 1 and 4) removably coupled to and extending between the first and second docking members 22, 24. The connection member lo includes first and second receiving bores 112, 114 configured to slide over the respective first and second docking members 22, 24. As shown in FIGS. 1 and 4, the first and second receiving bores 112, 114 may each include a key or locking member 116, and the outer surfaces 44, 68 of the first and second docking members 22, 24 may each include a groove 118. The grooves 118 are configured to cooperate with the keys 116 to prevent relative rotational movement between the docking members 22, 24 and connection member 110. Various other arrangements are possible to achieve this same effect. For example, in an alternative embodiment, the first and second docking members 22, 24 may be provided with a key (not shown) while the first and second receiving bores 112, 114 may be provided with a groove (not shown). The connection member 110, may include two portions 110a, 110b configured to allow movement of the docking members 22, 24 relative to one another. The two portions 110a, 110b can be configured with respect to one another in any manner that allows for movement of the docking members 22, 24. For example, the two portions can be configured in a telescoping arrangement.

Figure 5:
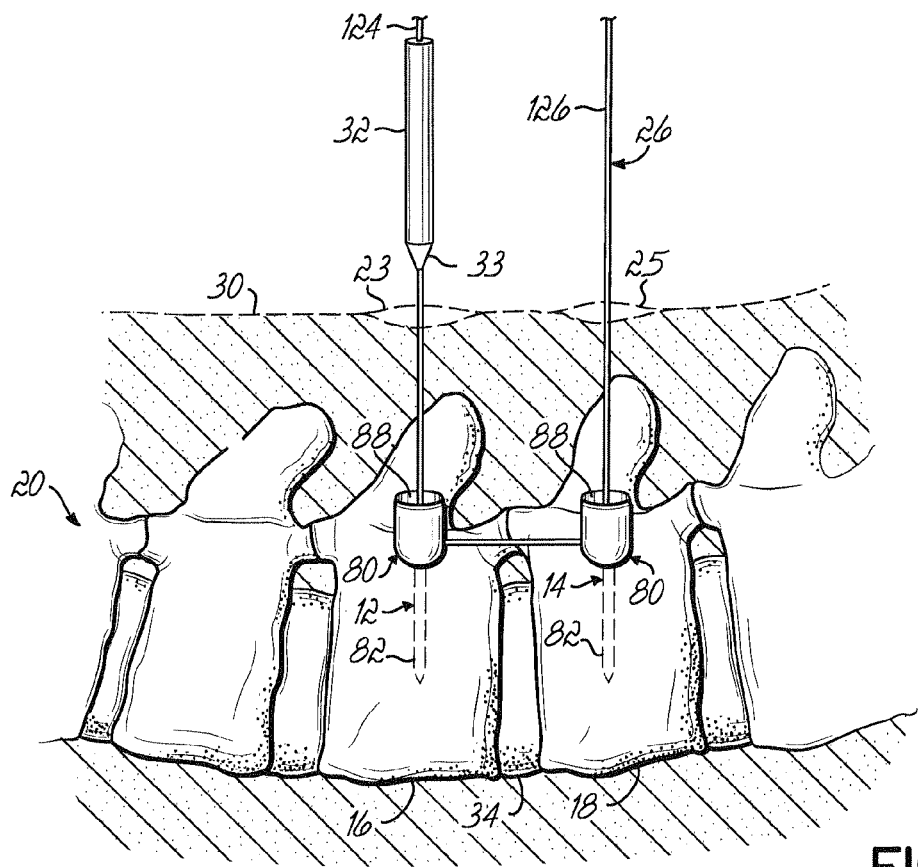
FIG. 5 is a schematic view showing a cross member inserted over the wire member after the first and second docking members have been removed from the system of FIG. 1.
Figure 6:
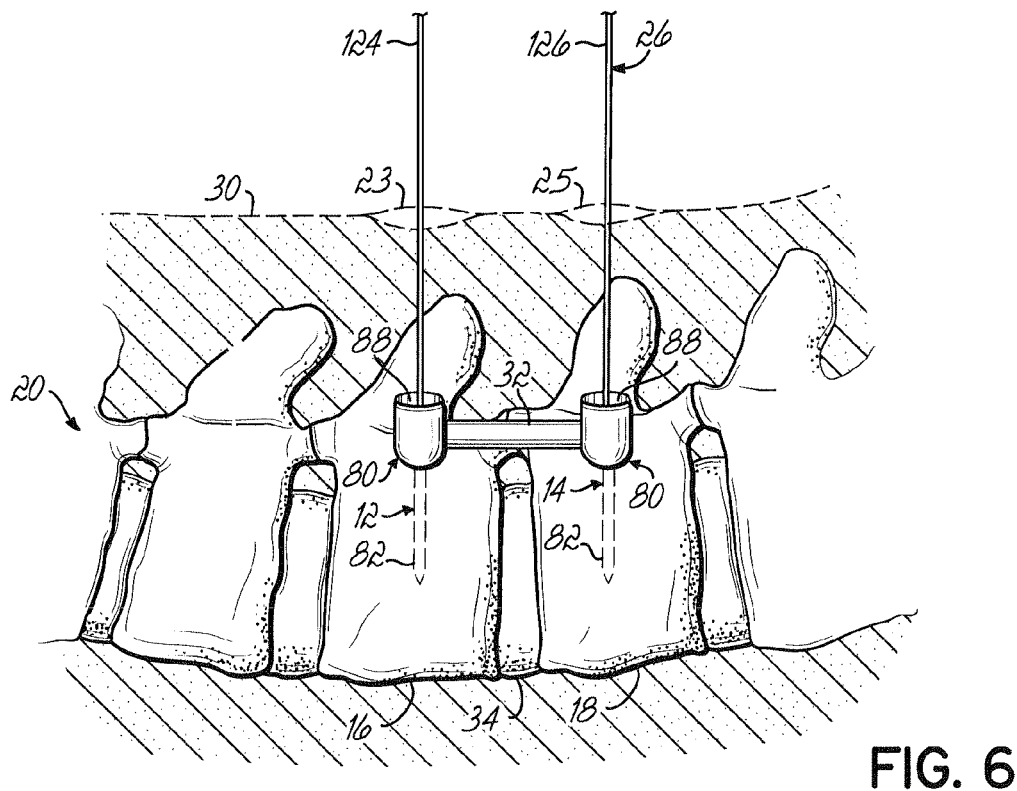
FIG. 6 is a schematic view shown the cross member of FIG. 5 positioned between the first and second anchor members.

The first and second docking members 22, 24 are ultimately removed from the patient's body 30 in accordance with the method described below, leaving wire member 26 positioned within the body 30. As shown in FIGS. 5 and 6, the system 10 may further include a cross member 32 configured to be guided alone the wire member 26 and secured to both the first and second anchor members 12, 14. The cross member 32 may be a cord, cable, rod, or any other suitable device for achieving the desired degree of spinal stabilization. For example, the cross member 32 may be rigid fixation rod or connector designed to hold the adjacent vertebrae in a desired position. Alternatively, the cross member 32 may be a flexible construct designed to provide dynamic stabilization. The spacer and cord in the Dynesys® Dynamic Stabilization System marketed by Zimmer, Inc. are one example of such a flexible construct.

Methods for minimally invasive surgery using one or more of the components in system 10 will now be described. The methods generally include creating a first access hole or channel 23 to a first location within the patient's body 30. The access channel may be created and maintained by any common surgical technique. For example, in manner not shown herein, the access channel may be created by making an incision and inserting a needle or dilator, and may be optionally maintained by a cannula, retractor, or the like. A first anchor member 12 is inserted through the first access channel to the first location within the patient's body 30. In the embodiment shown in FIGS. 1, 5, and 6, the first anchor member 12 is secured into position by securing the pedicle screw 82 into the pedicle of the vertebra 16. In other embodiments, vertebral anchors such as hooks or other devices can be used instead of pedicle screws. A second access hole or channel 25 is then created to a second location within the patient's body 30, and the second anchor member 12 is inserted through the second access channel and secured to the vertebra 18 in a similar manner.

With the first and second anchor members 12, 14 in place, the first and second docking members 22, 24 may then be inserted through the first and second access channels. Each docking member 22, 24 is inserted until the associated bottom portion 96, 100 is received in the retainer 80 of the corresponding anchor member 12, 14 (FIG. 1). More specifically, the first docking member 22 is inserted until the bottom portion 96 is received in the socket 88 of the retainer 80, and the second docking member 24 is inserted until the bottom portion 100 is received in a similar manner by the second anchor member 14. The docking members 22, 24 may be inserted into the patient's body 30 one at a time or simultaneously. In alternative embodiments, the first and second anchor members 12, 14 may be coupled to the first and second docking members 22, 24 prior to insertion into the access holes 23, 25. The docking members 22, 24 may be used to drive or attach the anchor members 12, 14 to or into the adjacent vertebra 16, 18.

The methods also include aligning the opening 46 on the outer surface 44 of the first docking member 22 with the opening 70 on the outer surface 68 of the second docking member 24. This step may be accomplished before or after the first and second docking members 22, 24 are inserted into the patient's body 30. In one embodiment, the openings 46, 70 are aligned by removably coupling the connection member 110 to the first and second docking members 22, 24. The first and second receiving bores 112, 114 of the connection member 110 may be slid over the respective first and second docking members 22, 24. To do so, however, the first and second docking members 22, 24 must first be rotated so that the grooves 118 on the respective outer surfaces 44, 68 are aligned with the keys 116 in the first and second receiving bores 112, 114. Such a step aligns the openings 46 and 70 and, after placing the connection member 110 over the docking members 22, 24, prevents relative rotation between the components.

Once the openings 46 and 70 are aligned, the wire member 26 is inserted into the first access channel and through the bore 48 in the first docking member 24. The wire member 26 bends as it travels through the bore 48 so that it is directed in a controlled manner toward the opening 70 on the second docking member 24 as it exits the opening 46. Sufficient force is applied to the wire member 26 to advance it through any tissue positioned between the first and second anchor members 12, 14. The end that engages the tissues of the patient or leading end 27 of the wire member 26 can be shaped or designed for improved passage through tissue. For example, the leading end 27 of wire member 26 may be shaped with a rounded or cone-shaped end, like leading end 33 of cross member 32. This type of leading end 27 may also improve engagement of wire member 26 with opening 70. Eventually, the wire member 26 is received through the opening 70 on the second docking member 24 and into the bore 72. The bore 72 then directs the wire member 26 to the opening 62 so that the wire member 26 may exit the second access channel. Alternatively, various tools may be inserted into the bore 72 to pull the wire member 26 through the second docking member 24 and out of the second access channel. This latter step may be necessary if the bore 72 is simply a cannula.

After the wire member 26 has been properly positioned within the patient's body 30, the first and second docking members 22, 24 may be removed from the respective first and second access channels. Forces exerted by tissue surrounding the wire member 26, especially between the first and second anchor members 12, 14, help maintain the wire member 26 within the patient's body 30 during this removal. In other words, although portions of the wire member 26 typically bend as the first and second docking members 22, 24 are removed, the forces exerted by the surrounding tissue generally maintain the wire member 26 between the first and second anchor members 12,14. A surgeon may also grip upper portions 124, 126 of the wire member 26 as the docking members 22, 24 are being removed to prevent the docking members 22, 24 from tugging or pulling the wire member 26 away from the anchor members 12,14.

With the first and second docking members 22, 24 removed, a cross member 32, such as a rigid or semi-rigid rod or flexible cord, may then be guided over the wire member 26. The cross member 32 is guided along the wire member 26 until it extends between the first and second anchor members 12, 14, as shown in FIG. 6. The ends of the cross member 32 are advantageously located proximate or within the retainers 80 of the first and second anchor members 12, 14. If necessary, manipulation tools (not shown) may be inserted through the first and second access channels to further adjust the position of the cross member 32 relative to the first and second anchor members 12, 14. Thus, even if portions of the wire member 26 are shifted slightly away from the first and second anchor members 12,14 as the docking members 22, 24 are removed, the wire member 26 remains sufficiently extended across the adjacent vertebrae 16, 18 to guide the cross member 32 between the first and second access channels. This allows the cross member 32 to be further adjusted without significant cutting or disruption of tissue.

The cross member 32 is then secured to the first and second anchor members 12, 14 using conventional fasteners and techniques. For example, set screws or nuts (not shown) may be inserted through the first and second access channels and secured to the first and second anchor members 12, 14 in a manner that clamps or locks the cross member 32. Alternatively, specially designed connectors (not shown) may be inserted through the access channels to secure the cross member 32.

The systems and methods described above therefore enable a cross member 32 to be secured between first and second anchor members 12, 14 without having to make large incisions or disrupting significant amounts of tissue. The systems and methods are particularly advantageous because they make use of the access channels already established to insert the first and second anchor members 22, 24. By reducing the amount of skin and tissue that must be cut, removed, and/or repositioned, the systems and methods help reduce the amount of blood loss, scarring, post-operative pain, and recovery time associated with more invasive procedures.

While the invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. For example, the systems and methods described above may be used to position one or more cross members 32 over more than two vertebra. The invention in its broader aspects is therefore not limited to the specific details, representative apparatus and methods and illustrative examples shown and described. Accordingly, departures may be made from such details without departing from the scope or spirit of the inventor's general inventive concept.

What is claimed is:

1. A system for installing a cross member between first and second anchor members within a patient's body using a wire member, the system comprising:

first and second docking members configured to be removably coupled to the first and second anchor members substantially along respective first and second axes, each docking member having a first end with an opening, a second end, a body extending between the first and second ends, the body having an outer surface with an opening, and a bore extending from the opening on the first end to the opening on the outer surface; and a wire member, the wire member configured to extend into the opening in the first end of the first docking member, through the bore in the first docking member, out the opening in the outer surface of the first docking member, into the opening in the outer surface of the second docking member, through the bore of the second docking member, and out the opening in the first end of the second docking member;

wherein the opening on the outer surface of the first docking member is configured to be aligned with the opening on the outer surface of the second docking member, the bore in the first docking member being configured to direct the wire member from the opening on the first end, through the body, and out the opening on the outer surface of the first docking member toward the opening on the outer surface of the second docking member, the first docking member and wire member configured for controlled direction of the wire member from the opening of the outer surface of the first docking member.

2. The system of claim 1 wherein the bore in the first docking member is defined by an axial portion extending from the opening on the first end toward the second end and a transverse portion extending from the axial portion to the opening on the outer surface.

3. The system of claim 2 wherein the bore in the second docking member includes an axial portion extending from the opening on the first end toward the second end and a transverse portion extending from the axial portion to the opening on the outer surface.

4. The system of claim 1, further comprising:

a connection member removably coupled to and extending between the first and second docking members.

5. The system of claim 4 wherein the connection member is configured to maintain the opening on the outer surface of the first docking member in alignment with the opening on the outer surface of the second docking member.

6. The system of claim 5 wherein the connection member includes first and second receiving bores configured to receive the respective first and second docking members, the first and second receiving bores each having a key and the outer surface of each docking member having a groove configured to cooperate with the corresponding key to prevent relative rotation between the docking member and connection member.

7. The system of claim 1 wherein the opening on the outer surface of the second docking member is larger than the opening on the outer surface of the first docking member.

8. A minimally invasive spinal surgery system for positioning components within in a patient's body, the system comprising:
    first and second anchor members;
    first and second docking members configured to be removably coupled to the respective first and second anchor members, each docking member having a first end with an opening, a second end, a body extending between the first and second ends, the body having an outer surface with an opening, and a bore extending from the opening on the first end to the opening on the outer surface, wherein the opening on the outer surface of the first docking member is configured to be aligned with the opening on the outer surface of the second docking member;
    a wire member configured to be inserted through the bore in the first docking member and received in the bore of the second docking member, the first and second docking members being removable from the wire member after the wire member is positioned within the patient's body; and
    a cross member having a central bore configured to be guided over the wire member after the first and second docking members are removed, the cross member further configured to be secured to both the first and second anchor members.

9. The system of claim 8 wherein the first and second anchor members each comprise:
    a pedicle screw having a shaft portion and a head portion; and
    a cup-shaped retainer defining a socket with top and bottom ends, the top end being open and the bottom end having a bore sized to retain the head portion of the pedicle screw within the socket while allowing the shaft portion to extend there through.

10. The system of claim 9 wherein the respective bodies of the first and second docking members each have a bottom portion at the second end configured to be received in the socket of the retainer of the corresponding anchor member.

11. The system of claim 8 wherein the cross member is a flexible construct configured to provide dynamic stabilization.

12. The system of claim 8 wherein the cross member is a rigid rod for spinal fixation.

13. The system of claim 8 wherein the wire member is a guidewire constructed from nickel titanium.

14. The system of claim 8 wherein the respective bores in the first and second docking members are each defined by an axial portion extending from the opening on the first end toward the second end and a transverse portion extending from the axial portion to the opening on the outer surface.

15. The system of claim 8, further comprising:
    a connection member removably coupled to and extending between the first and second docking members.

16. The system of claim 15 wherein the connection member is configured to maintain the opening on the outer surface of the first docking member in alignment with the opening on the outer surface of the second docking member.

17. The system of claim 16 wherein the connection member includes first and second receiving bores configured to receive the respective first and second docking members, the first and second receiving bores each having a key and the outer surface of each docking member having a groove configured to cooperate with the corresponding key to prevent relative rotation between the docking member and connection member.

18. A method for minimally invasive surgery, comprising the steps of:
    creating a first and second access channels extending to respective first and second locations within a patient's body;
    inserting first and second anchor members in the patient's body through the respective first and second access channels;
    inserting first and second docking members into the patient's body through the respective first and second access channels, each docking member having a first end with an opening, a second end, a body extending between the first and second ends, the body having an outer surface with an opening, and a bore extending from the opening on the first end to the opening on the outer surface;
    aligning the opening on the outer surface of the first docking member with the opening on the outer surface of the second docking member; and
    inserting a wire member into the opening in the first end of the first docking member, through the bore in the first docking member, out the opening in the outer surface of the first docking member, into the opening in the outer surface of the second docking member, through the bore of the second docking member, and out the opening in the first end of the second docking member.

19. The method of claim 18, further comprising:
    removing the first and second docking members while maintaining the wire member within the patient's body;
    guiding a cross member over the wire member until the cross member extends between the first and second anchor members; and
    securing the cross member to the first and second anchor members.

20. The method of claim 18 wherein the outer surface of each docking member includes a groove, and aligning the opening on the outer surface of the first docking member further comprises:
    removably coupling a connection member to the first and second docking members, the connection member having first and second receiving bores configured to receive the respective first and second docking members, the first and second receiving bores configured to cooperate with the corresponding docking member to prevent relative rotation between the receiving bore and docking member.

21. The method of claim 18, further comprising:
    assembling the first and second anchor members to the first and second docking members prior to insertion into the patient's body.

* * * * *